US00PP07946P

United States Patent [19]

Warriner

[11] Patent Number: Plant 7,946

[45] Date of Patent: Aug. 18, 1992

[54] ROSE PLANT JACCOR

[75] Inventor: William A. Warriner, Tustin, Calif.

[73] Assignee: Bear Creek Gardens, Inc., Medford, Oreg.

[21] Appl. No.: 625,928

[22] Filed: Dec. 10, 1990

[51] Int. Cl.[5] ..... A01H 5/00

[52] U.S. Cl. ..... Plt./18

[58] Field of Search ..... Plt./11, 18, 19

*Primary Examiner*—Howard J. Locker

*Attorney, Agent, or Firm*—Klarquist, Sparkman, Campbell, Leigh and Whinston

[57] ABSTRACT

A hybrid tea class rose having strong fragrance, large open flowers and long pointed buds, thick petals, long stems, very vigorous upright growth and novel coral pink flower color.

1 Drawing Sheet

The present invention relates to a new and distinct variety of rose plant of the hybrid tea class which was originated by me by crossing an unnamed seedling, with the variety Showstopper, U.S. Plant Pat. No. 4,851.

The primary objective of this breeding was to produce a new rose variety having the large fragrant flower of the seedling parent coupled with the long stems and high production of Showstopper. The objective was substantially achieved along with other desirable improvements as evidenced by the following unique combination of characteristics which are outstanding in the new variety and which distinguish it from its parents, as well as from all other varieties of which I am aware:

1. Strong fragrance.
2. Large open flower and long pointed buds.
3. Thick petals.
4. Long stems for a garden rose (18 to 22")
5. Very vigorous upright growth.
6. Novel coral pink flower color.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage:

*Seed parent.*—Unnamed seedling.

*Pollen parent.*—Showstopper, U.S. Plant Pat. No. 4,851.

Classification:

*Botanical.*—*Rosa hybrida.*

*Commercial.*—Hybrid tea.

FLOWER

Observations made from specimens grown in a garden environment in Somis, Calif., in September 1990.

Blooming habit: Recurrent.

Bud:

*Size.*—2 to 2½ inches when the petals start to unfurl.

*Form.*—Very long, pointed ovoid.

*Color.*—When sepals first divide, bud color is Red Group 48B. When half blown, the upper sides of the petals are Red 49B at the center of the flower with outer petals Red Group 48B; and the lower sides of the petals are Red Group 49B.

*Sepals.*—Color: Green Group 138C. Surface texture: Covered with fine hairs. There are three normally appendaged sepals. There are two unappendaged sepals with hairy edges.

*Receptacle.*—Color: Green Group 138B. Shape: Funnel. Size: Medium (5/16"×5/16"). Surface: Smooth.

*Peduncle.*—Length: Medium (3"). Surface: Glandular. Color: Bronzy. Strength: Stiff, erect.

Bloom:

*Size.*—Very large. Average open size is 5 to 6 inches.

*Borne.*—Singly.

*Stems.*—Long (18 to 22"), strong.

*Form.*—When first open: High center. Permanence: Retains its form to the end, outer petals curl back.

*Petalage.*—Number of petals under normal conditions: 30 to 35.

*Color.*—The upper side of the petals is Red Group 49B, darkening to Red Group 48B on the petals situated on the outside edge of the flowers. The reverse side of the petals is Red Group 49B. The base of each petal has a yellow half moon at the point of attachment (⅜"×⅜"). The major color on the upper side is Red Group 49B.

*Variegations.*—None.

*Discoloration.*—No change in the general tonality at the end of the first day. Little change at the end of the third day. In very bright conditions, darkening of petal edges throughout flower can occur.

*Fragrance.*—Strong.

Petals:

*Texture.*—Thick, leathery.

*Shape.*—Deltoid.

*Form.*—Tips slightly recurved, edges slightly quilled.

*Arrangement.*—Imbricated, with no petaloids in the center.

*Persistence.*—Drop off cleanly.

*Lastingness.*—On the plant: Long (5 days). As a cut flower: Long (5 to 7 days).

Reproductive parts:

*Anthers.*—Size: Large. Quantity: Many. Color: Reddish brown. Arrangement: Regular around styles.

*Filaments.*—Color: Reddish brown.

*Pollen.*—Color: Lemon yellow.

*Styles.*—Color: Deep red.

*Stigmas.*—Color: Greenish white.

Form: Bush.

Growth: Very vigorous, upright, branching.

Foliage:

*Number of leaflets on normal mid-stem leaves.*—5.

*Size.*—Large (5½"×4").

*Quantity.*—Abundant.

*Color.*—New foliage: Bronze-red. Old foliage: Dark green.

Leaflets:

*Shape.*—Pointed oval.

*Texture.*—Upper side: Smooth.

*Edge.*—Serrated.

*Serration.*—Single, small.

*Petiole rachis.*—Color: Green.

*Petiole underside.*—Rough, with prickles.

*Stipules.*—Medium (½"), bearded.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked downward.

*Color when young.*—Red.

Small prickles:

*Quantity.*—Few on main stalk and on laterals.

*Color.*—Green.

I claim:

1. A new and distinct variety of rose plant of the hybrid tea class, substantially as herein shown and described, characterized particularly as to novelty by the unique combination of its long bud, large open flower, thick petals, strong fragrance, vigorous growth, unusual flower color and excellent cutting stems.

* * * * *

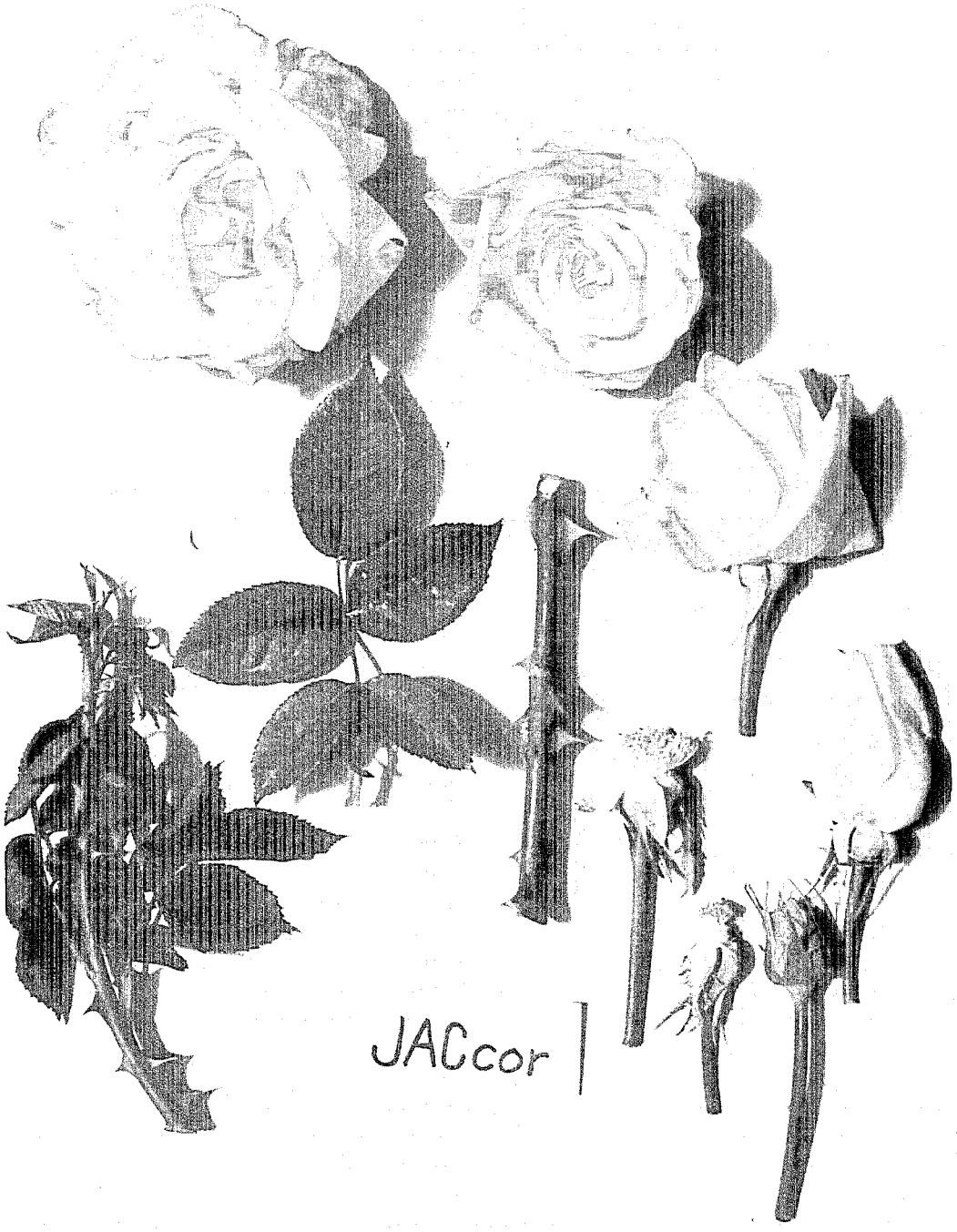
JACcor